United States Patent [19]

Fischer et al.

[11] B 4,001,292
[45] Jan. 4, 1977

[54] SULFITES OF AROMATIC GLYCOLIC AMIDES

[75] Inventors: Adolf Fischer, Mutterstadt; Hanspeter Hansen, Ludwigshafen; Wolfgang Rohr, Mannheim, all of Germany

[73] Assignee: BASF Aktiengesellschaft, Ludwigshafen (Rhine), Germany

[22] Filed: July 1, 1974

[21] Appl. No.: 484,419

[44] Published under the second Trial Voluntary Protest Program on March 9, 1976 as document No. B 484,419.

[30] Foreign Application Priority Data

July 7, 1973  Germany .......................... 2334715

[52] U.S. Cl. .............................. 260/456 NS; 71/103
[51] Int. Cl.$^2$ ..................................... C07C 137/00
[58] Field of Search ........................... 260/456 NS

[56] References Cited

UNITED STATES PATENTS 2,917,502  12/1959  Schwyzer et al. ............ 260/456 NS

OTHER PUBLICATIONS

Baker et al., Chem. Abstract, 64, 651h (1966).

Primary Examiner—James O. Thomas, Jr.
Assistant Examiner—Nicky Chan
Attorney, Agent, or Firm—Johnston, Keil, Thompson & Shurtleff

[57] ABSTRACT

New and valuable sulfites of glycolic anilides having a good herbicidal action, and a process for controlling the growth of unwanted plants with these compounds.

4 Claims, No Drawings

SULFITES OF AROMATIC GLYCOLIC AMIDES

The present invention relates to new and valuable sulfites of aromatic glycolic amides, herbicides containing them, and the use of these compounds as herbicides.

It is known to use N-isopropyl-α-chloroacetanilide for controlling unwanted plants in crops such as Indian corn, soybeans and vegetables. However, its action is not satisfactory.

We have now found that sulfites of aromatic glycolic amides of the formula

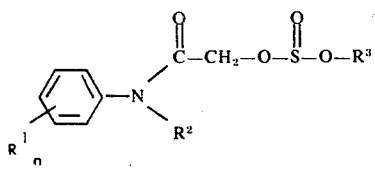

where $R^1$ denotes hydrogen, alkyl, e.g., methyl, ethyl, propyl and isopropyl, alkoxy, e.g., methoxy and ethoxy, haloalkyl, e.g., trifluoromethyl, or halogen, e.g., fluoro, chloro, bromo and iodo, $n$ denotes one of the integers 0, 1, 2, 3 and 4, $R^2$ denotes an aliphatic or cycloaliphatic radical, e.g., methyl, ethyl, propyl, isopropyl, butyl, sec-butyl, tert.-butyl, allyl, propargyl, butynyl, e.g., butyn-1-yl-3, butenyl, cyclopentyl and cyclohexyl, or an araliphatic radical, e.g., benzyl, p-chlorobenzyl and 2-methylbenzyl, and $R^3$ denotes an aliphatic or cycloaliphatic radical of a maximum of 6 carbon atoms and which is unsubstituted or substituted by halogen or alkoxy, e.g., methyl, ethyl, propyl, isopropyl, butyl, sec-butyl, tert-butyl, allyl, propargyl, butynyl, e.g., butyn-1-yl-3, butenyl, β-chloroethyl, dichloroallyl, trichloroallyl, 2-methyl-3-dichloroallyl, 4-chlorobutyn-2-yl, cyclopropyl and cyclohexyl, have a good herbicidal action. When $n$ is greater than 1, $R^1$ may denote identical or different substituents. The new compounds have a better herbicidal action than N-isopropyl-α-chloroacetanilide.

The active ingredients may be prepared by reacting at 10° to 15°C, an alkyl chlorosulfinate with a glycolic amide in an inert solvent and in the presence of an agent which binds hydrogen chloride.

EXAMPLE 1

Preparation of N-methylacetanilido-(α-methylsulfite)

16.5 parts (by weight) of N-methyl-α-hydroxyacetanilide and 8.0 parts of dry pyridine are dissolved in 100 parts of benzene; at 10° to 15°C, a solution of 11.4 parts of methyl chlorosulfinate in 50 ccm of dry benzene is dripped in. After about 1 hour the pyridinium hydrochloride is removed by suction filtration and the organic phase washed with water. After drying, the solvent is distilled off.

The compound has the following structure:

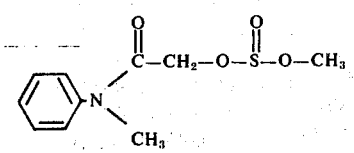

Boiling point (0.01 mm): 152° to 154°C.

The following compounds may be prepared by the same process:

N-methylacetanilido-(α-ethylsulfite)
N-methylacetanilido-(α-isopropylsulfite)
N-(butyn-1-yl-3)-acetanilido-(α-ethylsulfite)
N-(butyn-1-yl-3)-acetanilido-(α-isopropylsulfite)
N-(butyn-1-yl-3)-acetanilido-(α-methylsulfite), m.p.: 69° to 70°C
N-isopropylacetanilido-(α-methylsulfite), m.p.: 60° to 61°C
N-isopropylacetanilido-(α-isopropylsulfite), m.p.: 52° to 53°C
N-ethylacetanilido-(α-propylsulfite), $n_{25}^D$: 1.5295
N-ethylacetanilido-(α-isopropylsulfite), $n_{25}^D$: 1.5164
N-ethylacetanilido-(α-methylsulfite), $n_{25}^D$: 1.5118
N-ethylacetanilido-(α-ethylsulfite), $n_{25}^D$: 1.5010
N-methyl-(p-methoxyacetanilido)-(α-isopropylsulfite)
N-(butyn-1-yl-3)-(p-methoxyacetanilido)-(α-isopropylsulfite)
N-methyl-(p-methylacetanilido)-(α-isopropylsulfite)
N-(butyn-1-yl-3)-(p-methylacetanilido)-(α-isopropylsulfite)
N-(2-methylbenzyl)-acetanilido-(α-methylsulfite)
N-(2-methylbenzyl)-acetanilido-(α-ethylsulfite)
N-(2-methylbenzyl)-acetanilido-(α-propylsulfite)
N-(2-methylbenzyl)-acetanilido-(α-isopropylsulfite)
N-tert-butylacetanilido-(α-isopropylsulfite), m.p.: 78°C
N-tert-butylacetanilido-(α-methylsulfite), m.p.: 57°C
N-methylacetanilido-(α-sec-butylsulfite), $n_{25}$: 1.5083
N-(butyn-1-yl-3)-acetanilido-(α-isobutylsulfite), $n_{25}$: 1.5098
N-(butyn-1-yl-3)-acetanilido-(α-sec-butylsulfite), $n_{25}$: 1.5132
N-(butyn-1-yl-3)-acetanilido-(α-n-butylsulfite), $n_{25}$: 1.5172
N-isobutylacetanilido-(α-methylsulfite), $n_{25}$: 1.5229
N-isobutylacetanilido-(α-ethylsulfite), $n_{25}$: 1.5100
N-methylacetanilido-(α-n-butylsulfite), $n_{25}$: 1.5144
N-isobutylacetanilido-(α-isopropylsulfite), $n_{25}$: 1.5059
N-isobutylacetanilido-(α-isopropylsulfite), $n_{25}$: 1.5028.

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as
Cynodon spp.            Dactylis spp.
Digitaria spp.          Avena spp.
Echinochloa spp.        Bromus spp.
Setaria spp.            Uniola spp.
Panicum spp.            Poa spp.
Alopecurus spp.         Leptochloa spp.
Lolium spp.             Brachiaria spp.
Sorghum spp.            Eleusine spp.
Agropyron spp.          Cenchrus spp.
Phalaris spp.           Eragrostis spp.
Apera spp.              Phragmitres communis
etc.;
Cyperaceae, such as
Carex spp.              Eleocharis spp.
Cyperus spp.            Scirpus spp.

-continued dicotyledonous weeds, such as
Malvaceae, e.g.,
Abutilon theoprasti
Sida spp.
etc.;
Compositae, such as
Ambrosia spp.
Lactuca spp.
Senecio spp.
Sonchus spp.
Xanthium spp.
Iva spp.
Galinsoga spp.
Taraxacum spp.
Chrysanthemum spp.
Cirsium spp.
Convolvulaceae, such as
Convolvulus spp.
Ipomea spp.
etc.;
Cruciferae, such as
Barbarea vulgaris
Brassica spp.
Capsella spp.
Sisymbrium spp.
Thlaspi spp.
Sinapis arvensis
etc.;
Geraniaceae, such as
Erodium spp.
etc.;
Portulacaceae, such as
Portulaca spp.
Primulaceae, such as
Anagallis arvensis
etc.;
Rubiaceae, such as
Richardia spp.
Galium spp.
Scrophulariaceae, such as
Linaria spp.
Veronica spp.
Solanaceae, such as
Physalis spp.
Solanum spp.
etc.;
Urticaceae, such as
Urtica spp.
Violaceae, such as
Viola spp.
Zygophyllaceae, such as
Tribulus terrestris
Euphorbiaceae, such as
Mercurialis annua
Umbelliferae, such as
Daucus carota
Aethusa cynapium
Commelinaeae, such as
Commelina spp.
Labiatae, such as
Lamium spp.
etc.;
Leguminosae, such as
Medicago spp.
Trifolium spp.
Vicia spp.
etc.;
Plantaginaceae, such as
Plantago spp.
Polygonaceae, such as
Polygonum spp.
Rumex spp.
Aizoaceae, such as
Mollugo verticillata
Amaranthaceae, such as
Amaranthus spp.
Boraginaceae, such as
Amsinckia spp.
Myostis spp.
etc.;
Caryophyllaceae, such as
Stellaria spp.
Spergula spp.
Saponaria spp.
Scleranthus annus
Chenopodiaceae, such as
Chenopodium spp.
Kochia spp.
Salsola Kali
Lythraceae, such as
Cuphea spp.
Oxalidaceae, such as
Oxalis spp.

Hibiscus spp.
Malva spp.

Centaurea spp.
Tussilago spp.
Lapsana communis
Tagetes spp.
Erigeron spp.
Anthemis spp.
Matricaria spp.
Artemisia spp.
Bidens spp.
etc.;

Cuscuta spp.
Jaquemontia tamnifolia

Arabidopsis thaliana
Descurainia spp.
Draba spp.
Coronopus didymus
Lepidium spp.
Raphanus spp.

Geranium spp.

etc.;

Lysimachia spp.

Diodia spp.
etc.;

Digitalis spp.
etc.;

Nicandra spp.
Datura spp.

etc.;

etc.;

Euphorbia spp.

Ammi majus
etc.;

etc.;

Galeopsis spp.

Sesbania exaltata
Cassia spp.
Lathyrus spp.

etc.;

Fagopyrum spp.
etc.;

etc.;

etc.;

Anchusa spp.
Lithospermum spp.

Silene spp.
Cerastium spp.
Agrostemma githago
etc.;

Atriplex spp.
Monolepsis nuttalliana
etc.;

etc.;

-continued

Ranunculaceae, such as
Ranunculus spp.
Delphinium spp.
Papaveraceae, such as
Papaver spp.
etc.;
Onagraceae, such as
Jussiaea spp.
Rosaceae, such as
Alchemillia spp.
etc.;
Potamogetonaceae, such as
Potamogeton spp.
Najadaceae, such as
Najas spp.
Marsileaceae, such as
Marsilea quadrifolia Adonis spp.
etc.;

Fumaria officinalis etc.;

Potentilla spp.

etc.;

etc.;

etc.

The new active ingredients may be used in cereal crops such as

Avena spp.
Triticum spp.
Hordeum spp.
Secale spp.

Sorghum
Zea mays
Panicum miliaceum
Oryza spp.

and in dicotyledon crops such as

Cruciferae e.g.,
Brassica spp.
Sinapis spp.
Compositae, e.g.,
Lactuca spp.
Helianthus spp.
Malvaceae, e.g.,
Gossypium hirsutum
Leguminosae, e.g.,
Medicago spp.
Trifolium spp.
Pisum spp.
Chenopodiaceae, e.g.,
Beta vulgaris
Solanaceae, e.g.,
Solanum spp.
Nicotiania spp.
Linaceae, e.g.,
Linum spp.
Umbelliferae, e.g.,
Petroselinum spp.
Daucus carota
Rosaceae, e.g.,
Fragaria
Cucurbitaceae, e.g.,
Cucumis spp.
Liliaceae, e.g.,
Allium spp.
Vitaceae, e.g.,
Vitis vinifera
Bromeliaceae, e.g.,
Ananas sativus.

Raphanus spp.
Lepidium spp.

Carthamus spp.
Scorzonera spp.

Phaseolus spp.
Arachis spp.
Glycine max.

Spinacia spp.

Capsicum annuum

Apium graveolens

Cucurbita spp.

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before or after planting, before sowing, pre-emergence, during emergence, and postemergence.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or mineral origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients (if desired, immediately before use (tankmix)) oils of various types, herbicides, fungicides, nematocides, insecticides, bactericides, trace elements, fertilizers, antifoams (e.g., silicones), growth regulators, antidotes and other herbicidally effective compounds such as substituted anilines
substituted aryloxycarboxylic acids and salts, esters and amides thereof
substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridine carboxylic acids and their salts, esters and amides
substituted pyridines
substituted pyridine carboxylates
substituted pyridinones
substituted pyrimidines
substituted pyrimidones substituted pyrrolidine carboxylic acid and its salts, esters and amides substituted pyrrolidines substituted pyrrolidones substituted arylsulfonic acids and their salts, esters and amides substituted styrenes substituted tetrahydrooxadiazine diones substituted tetrahydroxadiazole diones substituted tetrahydromethanoindenes substituted tetrahydroxadiazole thiones substituted tetrahydrothiadiazine thiones substituted tetrahydrothiadiazole diones substituted aromatic thiocarbonylamides substituted thiocarboxylic acids and their salts, esters and amides substituted thiol carbamates substituted thioureas substituted thiophosphoric acids and their salts, esters and amides substituted triazines substituted triazoles substituted uracils, and substituted uretidine diones.

The last-mentioned herbicidal compounds may also be applied before or after the active ingredients or compositions thereof according to the invention.

These agents may be added to the herbicides according to the invention in a ratio by weight of from 1 : 10 to 10 : 1. The same applies to oils, fungicides, nematocides, insecticides, bactericides, antidotes and growth regulators.

EXAMPLE 2

In the greenhouse, loamy sandy soil was filled into pots and sown with various seeds. The soil prepared in this manner was then immediately treated with 3 kg per hectare of each of the following active ingredients (active ingredient VI being used for comparison purposes), each being dispersed or emulsified in 500 liters of water per hectare:

I 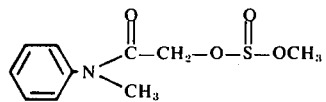

II 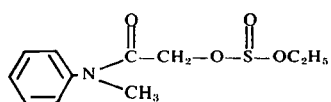

III 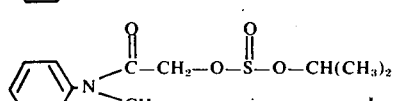

IV 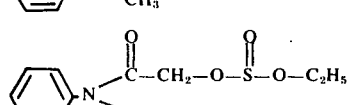

V 

VI 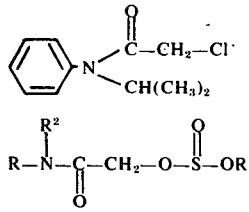

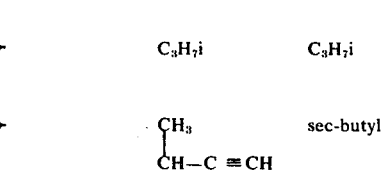

| | R | $R^2$ | $R^3$ |
|---|---|---|---|
| VII | 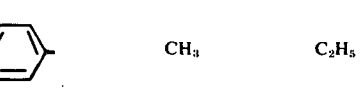 | $C_3H_7i$ | $C_3H_7i$ |
| VIII | 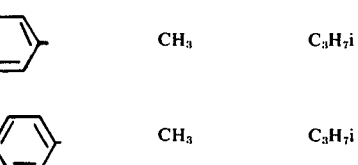 | $CH_3$ <br> $CH-C \equiv CH$ | sec-butyl |
| IX | 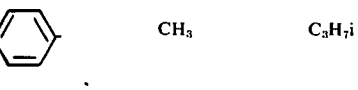 | $CH_3$ | $C_2H_5$ |
| X | 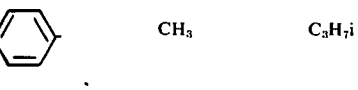 | $CH_3$ | $C_3H_7i$ |
| XI | 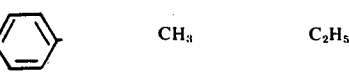 | $CH_3$ | $C_3H_7i$ |
| XII | 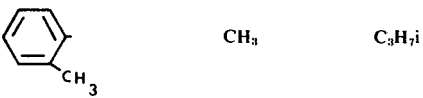 | $CH_3$ | $C_2H_5$ |
| XIII | 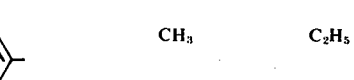 | $CH_3$ | $C_3H_7i$ |
| XIV | 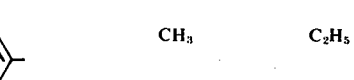 | $CH_3$ | $C_2H_5$ |

-continued

| | | | |
|---|---|---|---|
| XV | 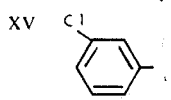 | CH₃ | C₃H₇i |
| XVI | 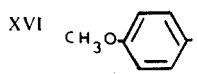 | CH₃ | CH₃ |

After 3 to 4 weeks it was ascertained that active ingredients I to XVI had a better herbicidal action than compound VI.

The results are given below:

| Active ingredient kg/ha | I 3 | II 3 | III 3 | IV 3 | V 3 | VI 3 |
|---|---|---|---|---|---|---|
| Crop plants: | | | | | | |
| Brassica napus | 0 | 0 | 0 | 0 | 0 | 0 |
| Glycine hispida | 0 | 0 | 0 | 0 | 0 | 0 |
| Zea mays | 0 | 0 | 0 | 0 | 0 | 0 |
| Gossypium hirsutum | 0 | 0 | 0 | 0 | 0 | 0 |
| Beta vulgaris | 0 | 0 | 0 | 0 | 0 | 0 |
| Unwanted plants: | | | | | | |
| Lolium perenne | 100 | 100 | 100 | 85 | 100 | 80 |
| Digitaria sanguinalis | 80 | 100 | 100 | 80 | 100 | 70 |
| Setaria viridis | 80 | 100 | 100 | 80 | 100 | 70 |
| Poa trivialis | 100 | 100 | 100 | 85 | 100 | 80 |
| Poa annua | 100 | 100 | 100 | 85 | 100 | 75 |

| Active ingredient kg/ha | VII 3 | VIII 3 | IX 3 | X 3 | XI 3 | XII 3 |
|---|---|---|---|---|---|---|
| Crop plants: | | | | | | |
| Brassica napus | 0 | 0 | 0 | 0 | 0 | 0 |
| Glycine max | 0 | 0 | 0 | 0 | 0 | 0 |
| Zea mays | 0 | 0 | 0 | 0 | 0 | 0 |
| Gossypium hirsutum | 0 | 0 | 0 | 0 | 0 | 0 |
| Beta vulgaris | 0 | 0 | 0 | 0 | 0 | 0 |
| Unwanted plants: | | | | | | |
| Lolium perenne | 80 | 90 | 95 | 100 | 90 | 85 |
| Digitaria sanguinalis | 80 | 80 | 90 | 95 | 90 | 85 |
| Setaria viridis | 90 | 80 | 90 | 95 | 90 | 90 |
| Poa trivialis | 90 | 90 | 95 | 100 | 90 | 80 |
| Poa annua | 95 | 95 | 100 | 100 | 90 | 90 |

| Active ingredient kg/ha | XIII 3 | XIV 3 | XV 3 | XVI 3 |
|---|---|---|---|---|
| Crop plants: | | | | |
| Brassica napus | 0 | 0 | 0 | 0 |
| Glycine max | 0 | 0 | 0 | 0 |
| Zea mays | 0 | 0 | 0 | 0 |
| Gossypium hirsutum | 0 | 0 | 0 | 0 |
| Beta vulgaris | 0 | 0 | 0 | 0 |
| Unwanted plants: | | | | |
| Lolium perenne | 85 | 80 | 90 | 95 |
| Digitaria sanguinalis | 80 | 75 | 85 | 90 |
| Setaria viridis | 90 | 75 | 90 | 95 |
| Poa trivialis | 80 | 80 | 85 | 90 |
| Poa annua | 85 | 80 | 90 | 95 |

0 = no damage
100 = complete destruction.

EXAMPLE 3

In the open, various plants were treated with 3 kg per hectare of each of active ingredients I to XVI (active ingredient VI being used for comparison purposes), each being emulsified in 500 liters of water per hectare.

After 3 to 4 weeks it was ascertained that active ingredients I to XVI had a better herbicidal action than compound VI.

The results are given below:

| Active ingredient kg/ha | I 3 | II 3 | III 3 | IV 3 | V 3 | VI 3 |
|---|---|---|---|---|---|---|
| Crop plants: | | | | | | |
| Brassica napus | 0 | 0 | 0 | 0 | 0 | 0 |
| Glycine hispida | 0 | 0 | 0 | 0 | 0 | 0 |
| Zea mays | 0 | 0 | 0 | 0 | 0 | 0 |
| Gossypium hirsutum | 0 | 0 | 0 | 0 | 0 | 0 |
| Beta vulgaris | 0 | 0 | 0 | 0 | 0 | 0 |
| Unwanted plants: | | | | | | |
| Lolium multiflorum | 80 | 100 | 100 | 100 | 100 | 40 |
| Lolium perenne | 85 | 100 | 100 | 100 | 100 | 40 |
| Echinochloa crus-galli | 100 | 100 | 60 | 100 | 100 | 30 |
| Digitaria sanguinalis | 100 | 100 | 60 | 100 | 100 | 35 |
| Setaria viridis | 100 | 100 | 60 | 100 | 100 | 35 |
| Poa trivialis | 85 | 100 | 100 | 100 | 100 | 45 |
| Poa annua | 85 | 100 | 100 | 100 | 100 | 50 |

| Active ingredient kg/ha | VII 3 | VIII 3 | IX 3 | X 3 | XI 3 | XII 3 |
|---|---|---|---|---|---|---|
| Crop plants: | | | | | | |
| Brassica napus | 0 | 0 | 0 | 0 | 0 | 0 |
| Glycine max | 0 | 0 | 0 | 0 | 0 | 0 |
| Zea mays | 0 | 0 | 0 | 0 | 0 | 0 |
| Gossypium hirsutum | 0 | 0 | 0 | 0 | 0 | 0 |
| Beta vulgaris | 0 | 0 | 0 | 0 | 0 | 0 |
| Unwanted plants: | | | | | | |
| Lolium perenne | 90 | 95 | 95 | 90 | 80 | 85 |
| Digitaria sanguinalis | 85 | 90 | 75 | 80 | 70 | 70 |
| Setaria viridis | 90 | 90 | 85 | 85 | 75 | 75 |
| Poa trivialis | 85 | 90 | 80 | 80 | 70 | 70 |
| Poa annua | 90 | 95 | 85 | 80 | 75 | 70 |
| Lolium multiflorum | 70 | 95 | 75 | 75 | 70 | 75 |
| Echinochloa crus-galli | 90 | 95 | 80 | 80 | 70 | 75 |

| Active ingredient kg/ha | XIII 3 | XIV 3 | XV 3 | XVI 3 |
|---|---|---|---|---|
| Crop plants: | | | | |
| Brassica napus | 0 | 0 | 0 | 0 |
| Glycine max | 0 | 0 | 0 | 0 |
| Zea mays | 0 | 0 | 0 | 0 |
| Gossypium hirsutum | 0 | 0 | 0 | 0 |
| Beta vulgaris | 0 | 0 | 0 | 0 |
| Unwanted plants: | | | | |
| Lolium perenne | 90 | 85 | 95 | 95 |
| Digitaria sanguinalis | 75 | 80 | 85 | 90 |
| Setaria viridis | 80 | 85 | 90 | 90 |
| Poa trivialis | 75 | 75 | 80 | 85 |
| Poa annua | 80 | 85 | 85 | 90 |
| Lolium multiflorum | 75 | 70 | 80 | 80 |
| Echinochloa crus-galli | 85 | 90 | 90 | 90 |

0 = no damage
100 = complete destruction

The action of the following compounds corresponds to that of compounds I to V and VII to XVI in Examples 2 and 3.

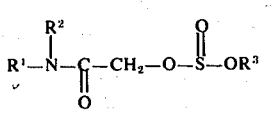

| R¹ | R² | R³ |
|---|---|---|
|  | CH₃ | C₄H₉n |
|  | CH₃ | CH₃ |
|  | CH₃ | C₄H₉n |

| Active ingredient kg/ha | I 3 | II 3 | III 3 | IV 3 | V 3 | VI 3 |
|---|---|---|---|---|---|---|
| ⟨benzene⟩-CH₃ (CH₃) | | | CH₃ | | C₂H₅ | |
| ⟨benzene⟩-CH₃ (CH₃) | | | CH₃ | | CH₃ | |
| ⟨benzene⟩-CH₃ (Cl) | | | CH₃ | | CH₃ | |

EXAMPLE 4

90 parts by weight of compound I is mixed with 10 parts by weight of N-methyl-α-pyrrolidone. A mixture is obtained which is suitable for application in the form of very fine drops.

EXAMPLE 5

20 parts by weight of compound II is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound III is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound IV is dissolved in a mixture consisting of 25 parts by weight of cyclohexanol, 65 parts by weight of a mineral oil fraction having a boiling point between 210° and 280°C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound V is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 9

3 parts by weight of compound VII is intimately mixed with 97 parts by weight of particulate kaolin. A dust is obtained containing 3% by weight of the active ingredient.

EXAMPLE 10

30 parts by weight of compound VIII is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:
1. A sulfite of an aromatic glycolic amide of the formula

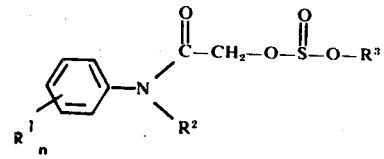

wherein R¹ is hydrogen or alkyl of 1 to 3 carbon atoms, $n$ is one of the integers 0, 1, 2, 3 and 4, R² is alkyl of 1 to 4 carbon atoms, and R³ is alkyl of up to 6 carbon atoms.
2. N-methylacetanilido-(α-methylsulfite).
3. N-methylacetanilido-(α-ethylsulfite).
4. N-methylacetanilido-(α-isopropylsulfite).

* * * * *